United States Patent [19]
Leahy et al.

[11] Patent Number: 5,640,977
[45] Date of Patent: Jun. 24, 1997

[54] APPARATUS AND METHOD FOR USE IN SURGERY

[75] Inventors: Patrick F. Leahy, Blackrock, Ireland; Berwyn M. Crook, Yardley; Robert D. Rambo, Sellersville, both of Pa.

[73] Assignee: Medical Creative Technologies, Inc., Colmar, Pa.

[21] Appl. No.: 300,346

[22] Filed: Sep. 2, 1994

[30] Foreign Application Priority Data

Apr. 8, 1994 [IE] Ireland .................. S940328

[51] Int. Cl.$^6$ .................. A61B 19/00
[52] U.S. Cl. .................. 128/897; 128/850; 606/215; 604/174
[58] Field of Search .................. 600/21–22; 128/897, 128/846, 850–856; 604/167, 174, 178, 237, 256; 606/213, 215

[56] References Cited

U.S. PATENT DOCUMENTS

| | | |
|---|---|---|
| 1,810,466 | 6/1931 | Deutsch . |
| 2,305,289 | 12/1942 | Coburg . |
| 2,835,253 | 5/1958 | Borgeson . |
| 3,111,943 | 11/1963 | Orndorff . |
| 3,244,169 | 4/1966 | Baxter . |
| 3,332,417 | 7/1967 | Blanford et al. . |
| 3,347,226 | 10/1967 | Harrower . |
| 3,347,227 | 10/1967 | Harrower . |
| 3,397,692 | 8/1968 | Creager et al. . |
| 3,416,520 | 12/1968 | Creager, Jr. . |
| 3,523,534 | 8/1970 | Nolan . |
| 3,841,332 | 10/1974 | Treacle . |
| 3,850,172 | 11/1974 | Cazalis . |
| 4,024,872 | 5/1977 | Muldoon . |
| 4,043,328 | 8/1977 | Cawood et al. . |
| 4,188,945 | 2/1980 | Wenander . |
| 4,367,728 | 1/1983 | Mutke . |
| 4,550,713 | 11/1985 | Hyman . |
| 4,553,537 | 11/1985 | Rosenberg . |
| 4,777,943 | 10/1988 | Chvapil . |
| 4,903,710 | 2/1990 | Jessamine et al. . |
| 4,926,882 | 5/1990 | Lawrence . |
| 4,991,593 | 2/1991 | LeVahn . |
| 4,998,538 | 3/1991 | Charowsky et al. . |
| 5,037,379 | 8/1991 | Clayman et al. . |
| 5,178,162 | 1/1993 | Bose . |
| 5,299,582 | 4/1994 | Potts . |
| 5,316,541 | 5/1994 | Fischer . |
| 5,514,133 | 5/1996 | Gozub et al. .................. 606/1 |

FOREIGN PATENT DOCUMENTS

WO95/24864  9/1995  WIPO .

*Primary Examiner*—John P. Lacyk
*Attorney, Agent, or Firm*—Howson and Howson

[57] ABSTRACT

Apparatus and method for hand-assisted minimally invasive laparoscopic surgery which allows for palpation and biophysical feedback within a sterile environment. A sleeve provides a sealed chamber communicating with a wound accessible to an surgeon's hand through entry and exit openings. The entry opening is sealed around the surgeon's wrist or forearm by a cuff.

31 Claims, 10 Drawing Sheets

APPARATUS AND METHOD FOR USE IN SURGERY

FIELD OF THE INVENTION

The present invention relates generally to apparatus and method for use in surgery, and more particularly to a surgical apparatus and method for permitting hand-assisted laparoscopic surgery and like minimally invasive procedures.

BACKGROUND OF INVENTION

Open surgery, in general, has been the surgeons' procedure of choice since it allows both hands access to the body cavity for bio/physical feedback through palpation of organs within the cavity. However, the relatively large incisions required can be traumatic for the patient and the healing process lengthy.

Many of these operations are now possible with minimally invasive laparoscopic surgical techniques using trocar and cannula assemblies, but they are not widely performed by surgeons trained only in conventional surgery. Highly specialized training and experience are required for such techniques. For example, in removing a dysfunctional organ or tissue from the abdominal cavity, the peritoneum must be cannulated at precisely located sites for insufflating the cavity and for inserting an endoscope and other surgical instruments. The instruments are manipulated within the cavity exclusively by observing their correlative positions on a TV monitor. Consequently, palpation and bio/physical feedback is not possible because there is no incision for the surgeon's hand to gain access to the cavity.

SUMMARY OF THE INVENTION

Accordingly, it is an object of the present invention to provide a surgical apparatus suitable for hand-assisted minimally invasive surgery which allows for palpation and biophysical feedback while retaining a controlled environment.

Another object of the invention is to provide a surgical apparatus which enables surgeons already trained in conventional open surgery to perform hand-assisted laparoscopic surgery with minimal additional training.

Another object is to provide a surgical apparatus which extends the range of operations that can be performed with relatively small incisions and minimal trauma to the patient.

Still another object is to provide a surgical apparatus which enables hand-access to an insufflated cavity without loss of pressure, which offers minimal risk of damage to the immune system, and which shortens the healing time and stay in a hospital.

A further object is to provide a surgical apparatus which can be easily applied to a patient for maintaining a sterile area around a wound.

A further object is to provide an easily operated cuff for positively sealing around an arm or instrument extending through an entry opening of a surgical enclosure.

A still further object is to provide a method for performing hand-assisted laparoscopic surgery.

These and other objects and novel features of the invention are accomplished with a surgical apparatus which is attached to a patient's body during surgical procedures for permitting a surgeon's hand access through an incision while maintaining an isolated and controlled environment in the abdominal cavity. One preferred embodiment comprises a sleeve having an entry opening at one end for receiving a hand and/or instrumentarium, an exit opening at the other end with an adhesive seal around the incision accessing a cavity in a patient's body. The entry opening is sealed by an inflatable cuff around the surgeon's arm to maintain a controlled environment within the sleeve when in use. A normally closed duckbill-like gas lock between the openings provides an antechamber for retaining pressure and environmental integrity in the abdominal cavity when the entry opening is breached. A separate wound protector may be installed at the exit opening and extend through the incision. In other embodiments, the entry opening is sealed by an adjustable tie clamp which tightens the sleeve around the arm; the sleeve provides a clear path between the entry and exit openings; the entry opening is sealed by a flexible cuff which closes around the arm by twisting one end relative to the other; the exit opening is sealed by flange on the open end of a surgeon's glove engaging a flange at the entry opening; and a integral wound protector is sealed around the exit opening for extending through an incision for lining the wall of the wound.

BRIEF DESCRIPTION OF THE DRAWINGS

The foregoing and other objects, novel features and advantages of the invention will become more apparent from the following description when taken in conjunction with the accompanying drawings wherein.

DESCRIPTION OF THE PREFERRED EMBODIMENTS

Figure 1:
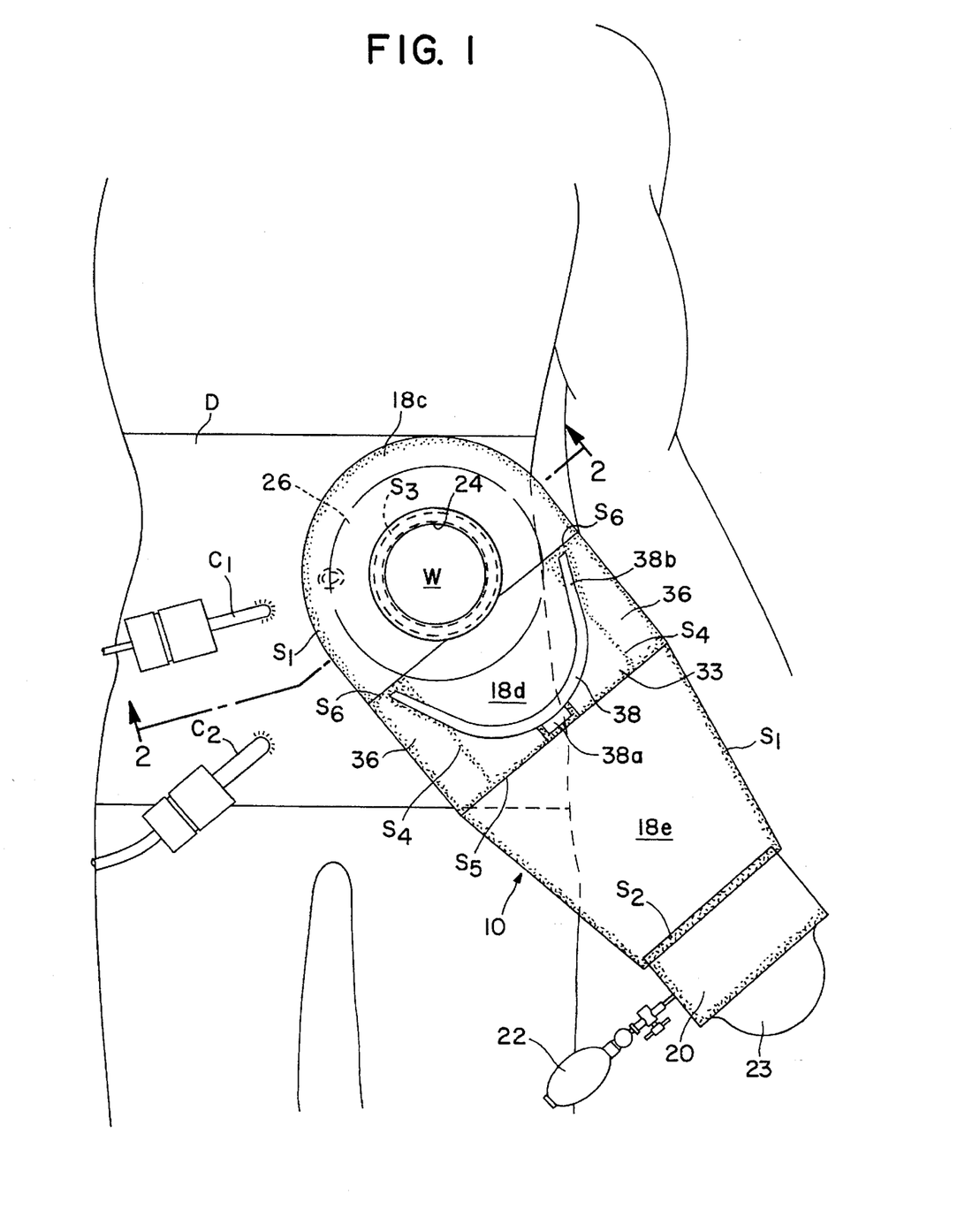
FIG. 1 represents one embodiment of a surgical apparatus with an integral inflatable cuff and separable wound protector according to the invention applied to the anterior wall of an insufflated abdomen of a patient undergoing laparoscopic surgery.
Figure 2:
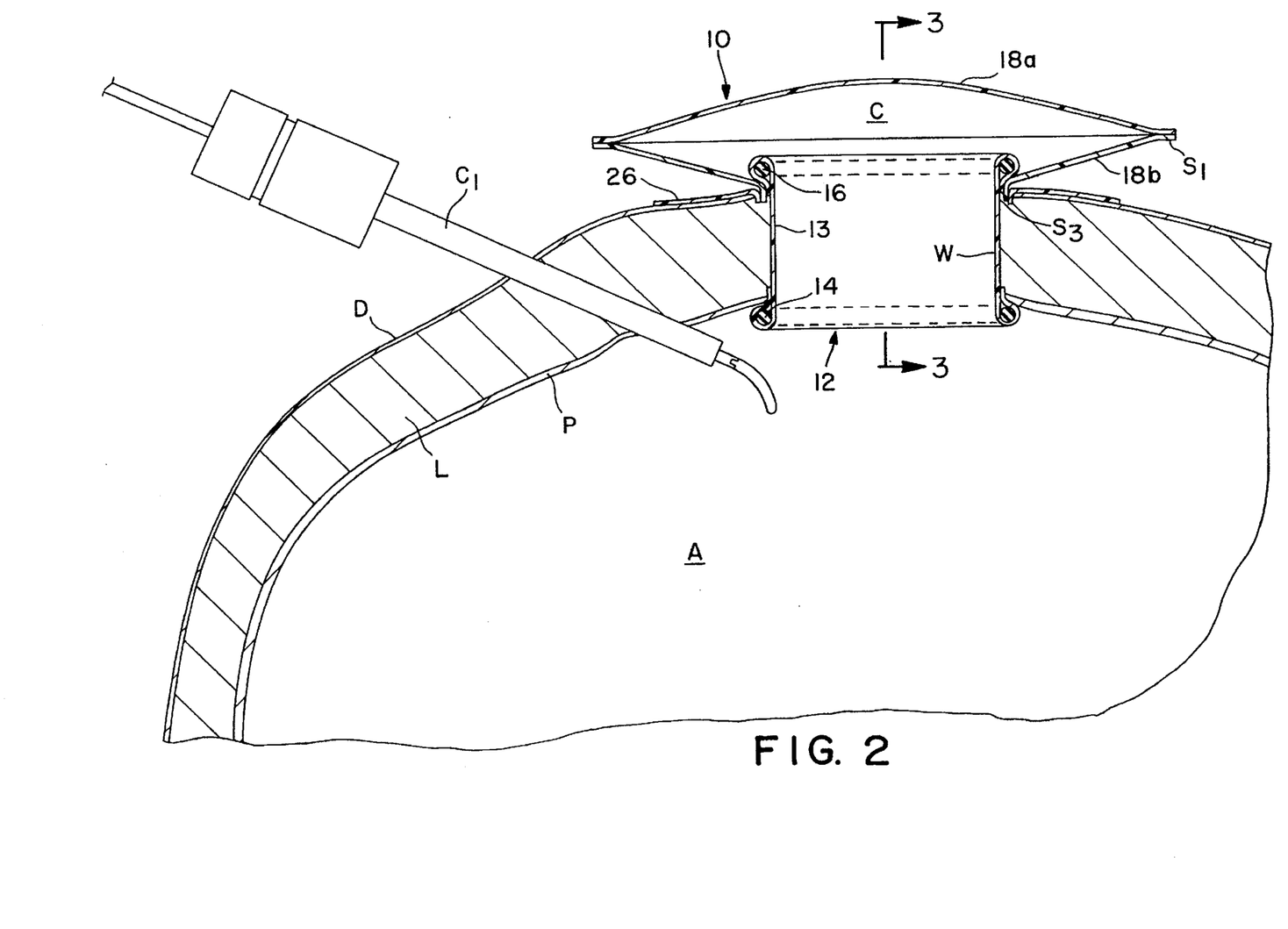
FIG. 2 is a view in transverse cross section of the surgical apparatus and the abdomen taken along the line 2—2 of FIG. 1.
Figure 3:
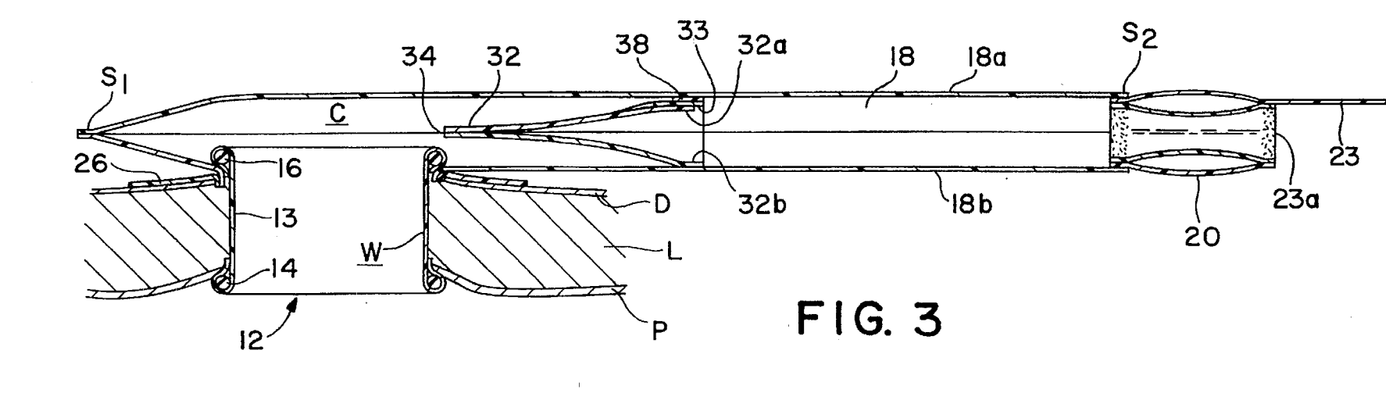
FIG. 3 is a view in longitudinal cross section of the surgical apparatus FIG. 1.

Referring now to the drawings wherein like reference characters denote like or corresponding parts throughout the several views, there is shown in FIGS. 1–3 one embodiment of a surgical apparatus 10 according to the invention. The apparatus 10 is shown adhered to an incise drape D with fenestration over a wound W in an insufflated abdominal cavity A of a patient. Cannulas $C_1$, $C_2$ extending into the cavity provide lumens for instrumentarium such as a trocar, insufflator, laparoscope and irrigator.

In brief, the apparatus 10 comprises an outer sleeve 18 having a distal portion 18c adapted to be positioned in proximity with a patient's body and a proximal portion 18e remote from the body. An axial entry opening 23a is provided at the proximal end 18e of the sleeve, and an lateral exit opening 24 is provided at the distal end 18c of the sleeve. A first sealing means to be described is provided for sealing the exit opening 24 at the distal end of the sleeve, and a second sealing means to be described is provided for sealing the entry opening 23a at the proximal end of the sleeve 18. A third sealing means to be described is provided in the sleeve for forming a valved chamber in communication with the exit opening 24.

As best seen in FIG. 1, the surgical apparatus 10 comprises an elongate outer sleeve 18 preferably made of a thin, transparent, gas-impermeable plastic sheet sufficiently supple for maneuvering ease i.e. enabling a wide range of arm movement at the entry opening 23a relative to the exit opening 24. A material found suitable for this purpose is a heat-sealable 3-mil polyolefin such as SARANEX® Film 2090 by The Dow Chemical Co. In a flat layout, sleeve 18 is constructed of congruent top and bottom panels 18a and 18b, respectively, defining a rounded distal section 18c, a straight intermediate section 18d and a tapered proximal section 18e. Panels 18a and 18b are heat-sealed together along a perimetric seam $S_1$ of section 18c and along the opposite sides of sections 18d and 18e. The proximal edge of tapered section 18e is heat sealed by a seam $S_2$ around an inflatable cuff 20 which is sealingly compressed in a toroidal shape around the surgeon's arm by a hand-operated elastic bulb inflator 22 to provide the second sealing means around the entry opening 23a of the proximal end of the sleeve 18. A tab 23 extending from the proximal end of cuff 20 provides a convenient grip for pulling the cuff over the hand and arm.

Figure 4:
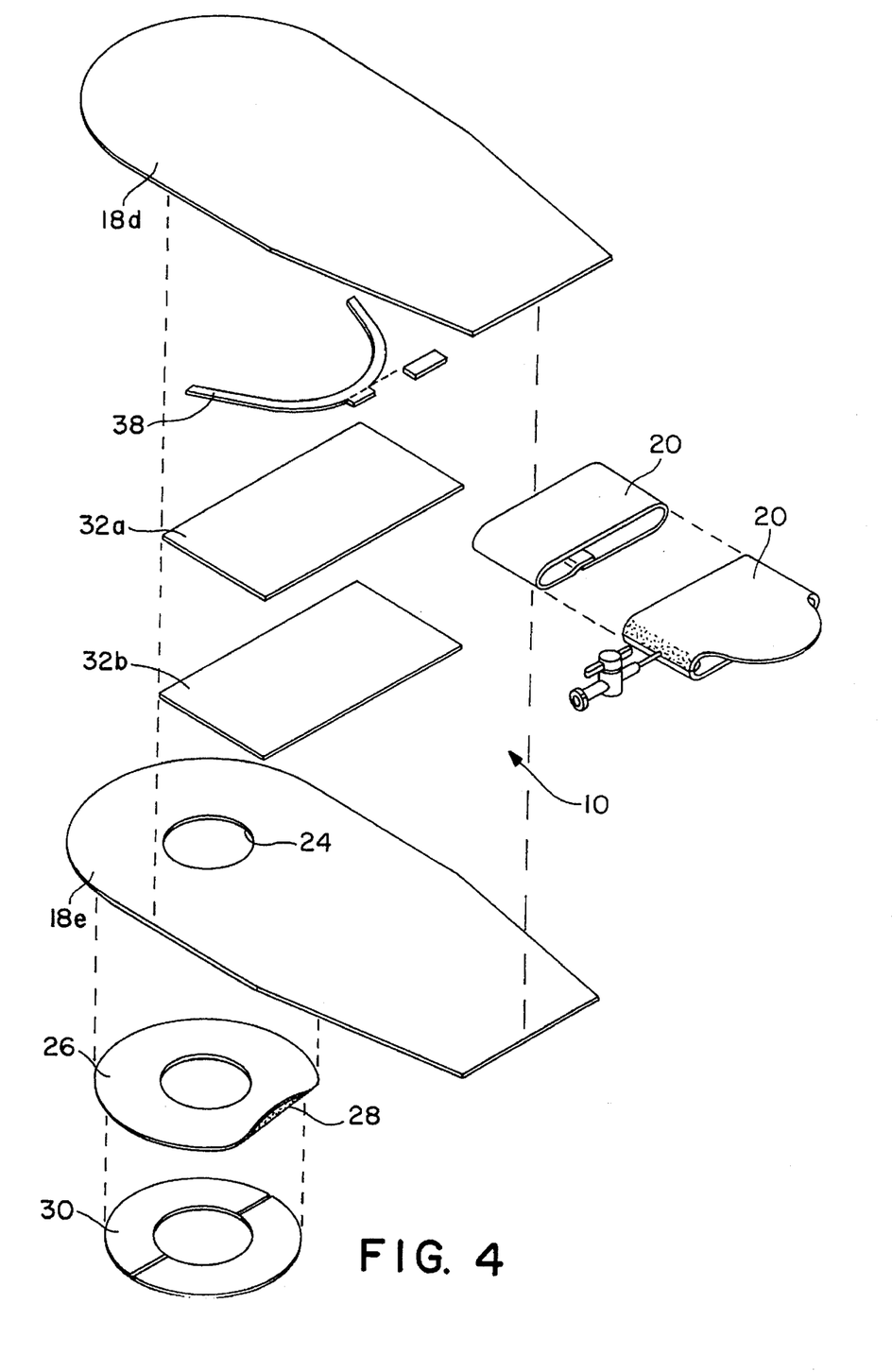
FIG. 4 is an exploded isometric view of principal components of the surgical apparatus of FIG. 1.

A lateral exit opening 24 is centrally located in rounded section 18c of bottom panel 18b and is sized to permit a surgeon's hand to pass into wound W. An annular flange 26, of like material as sleeve 18, is heat-sealed to the exposed side of bottom panel 18b by a seam $S_3$ around exit opening 24. A suitable adhesive 28 (FIG. 4) on the lower exposed side of flange 26 is completely covered prior to use by overlapping peel-off strips 30. When adhered to the patient's body, the flange 26 provides the first sealing means at the distal end of the sleeve 18.

The abdominal wall L and peritoneum P around wound W are protected from exposure to diseased tissue and non-sterile material during surgery by a wound protector 12. As best seen in FIGS. 2 and 3, the wound protector 12 comprises a thin flexible tube 13 and flexible O-rings 14 and 16 at opposite ends thereof. Tube 13 is longitudinally stretched over the entire peripheral surface of wound W by O-rings 14 and 16 which are expanded, respectively, over the internal edge surface of wound W and the inside surface of sleeve 18 around exit opening 24. Tube 13 is preferably made of a supple material impermeable to gases and microorganism-bearing fluids, and may be interiorly coated with a lubricant O-rings 14 and 16 are made of a compliant material such as silicon.

According to this embodiment of the invention, a third sealing means is provided in the sleeve 18 intermediate the first and second sealing means but closer to the distal end of the sleeve 18. To this end, the third sealing means includes an inner gas lock, or duckbill check valve 32 constructed of congruent upper and lower panels 32a and 32b, respectively, extending athwart straight section 18d and heat-sealed by seam $S_1$ along opposite sides thereof and by seams $S_4$ parallel-spaced from seam $S_1$ to form a normally closed aperture 34 (FIG. 3) of size sufficient for the surgeon's hand to pass through. The proximal edges of panels 32a and 32b are sealed, respectively, to top and bottom panels 18a and 18b along a seam $S_5$. Between seams $S_1$ and $S_4$, seam $S_5$ and a seam $S_6$ also seal, respectively, the distal and proximal edges of panels 32a and 32b together with both top and bottom panels 18a and 18b forming thereby pockets 36 on both sides of opening 33 and defining a gastight chamber C.

The distal end of aperture 34 is biased in a normally closed position by tension applied to opposite sides of check valve 32 by a bow-shaped stay 38 made of a thin strip of flexible material such as 30 mil thick high density polyethylene. A tab 38a extending from stay 38 intermediate opposed ends 38b thereof is heat-staked to the middle of panel 32a adjacent the proximal end thereof, and opposed ends 38b are respectively heat-staked in pockets 36 with the sides slightly bent in deflection toward panel 32b. Thus, gas lock 32 acts like a duckbill check valve to provide a sealed chamber C at wound W by restricting flow of insufflating gas from the area around wound W while the surgeon's hand or an instrument is being inserted or withdrawn through cuff 20. The interior of sleeve 18 and check valve 32 may be coated with a lubricant to reduce the friction and ease movement of the hand through port 34.

The size of surgical apparatus 10 may be varied to suit requirements. A typical sleeve 18 with inflatable cuff 20 is approximately 600 mm long, 240 mm wide at the distal and intermediate sections 18c and 18d, and 150 mm wide at the proximal end of section 18e. The diameters of exit opening 24 and OD of flange 26 are in the ranges of 8 mm–110 mm and 200 mm–240 mm respectively, and the width of check valve 32 is in the approximate range of 80 mm–110 mm. The diameter and length of wound protector tube 13 are in approximate ranges of 10 mm–200 mm and 30 mm–90 mm, respectively. Specific dimensions are determined according to the surgical procedure involved.

Figure 5:
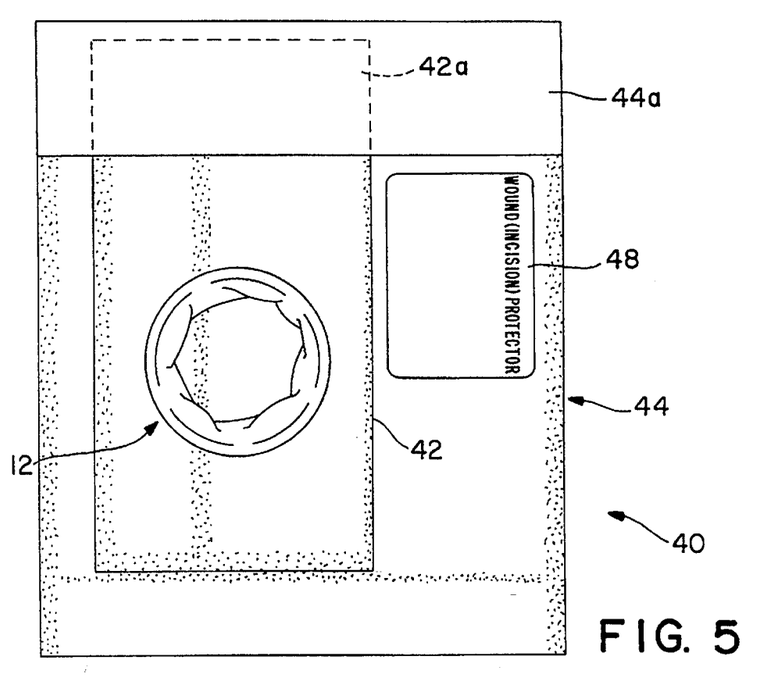
FIG. 5 illustrates the wound protector of FIG. 1 compacted in a sealed wrapper.
Figure 6:
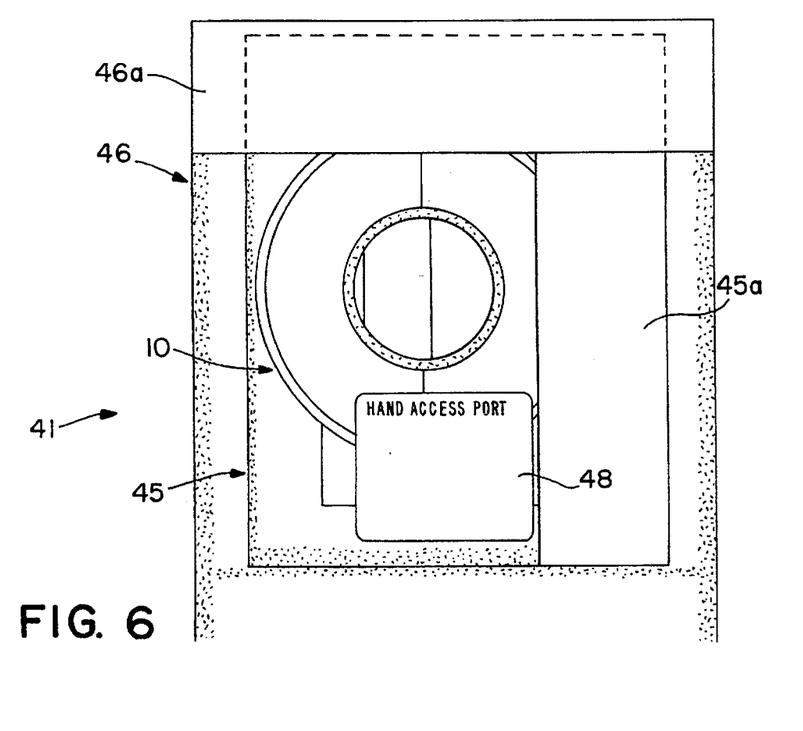
FIG. 6 illustrates the surgical apparatus of FIG. 1 folded flat in a sealed wrapper.

The apparatus 10 is conveniently stored in a sterile package. As best seen in FIGS. 5 and 6, prior to their use, the surgical apparatus 10 and wound protector 12 are separately folded in a flat form and stored in sealed packets 40 and 41, respectively. For example, a packet 40 containing wound protector 12 includes an inner bag 42 closed by a peel-seal flap 42a inserted within an outer bag 44 which is also closed by a peel-seal flap 44a. Surgical apparatus packet 41 is similarly contained in an inner bag 45 which is closed by a peel-seal flap 45a, and an outer bag 46 closed by a peel-seal flap 46a. Labels 48 affixed to each of packets 40 and 41 identify the contents and other information relevant to its use.

Figure 7:
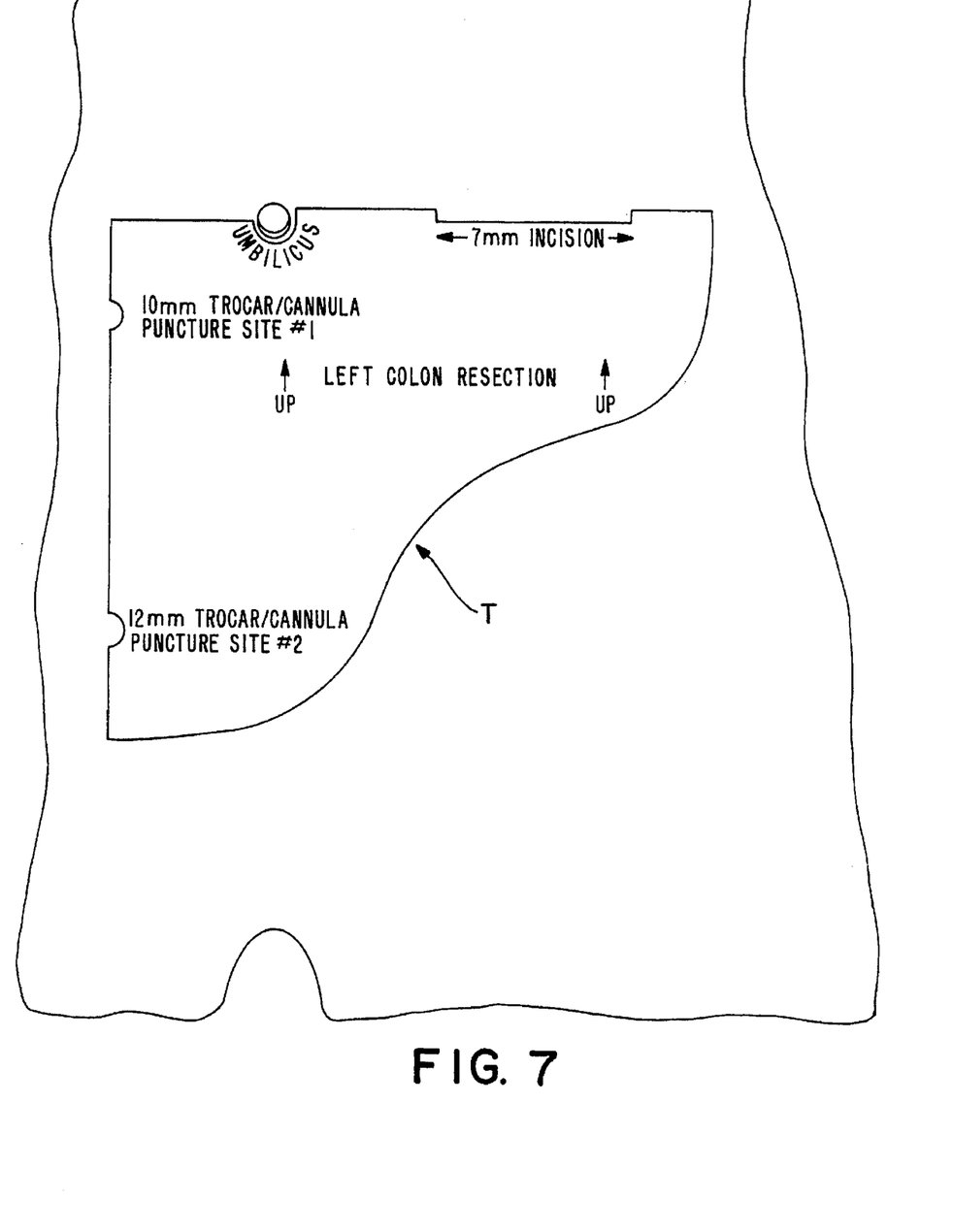
FIG. 7 represents a typical surgical template applied to the abdomen preceding laparoscopic surgery of FIG. 1.
Figure 8:
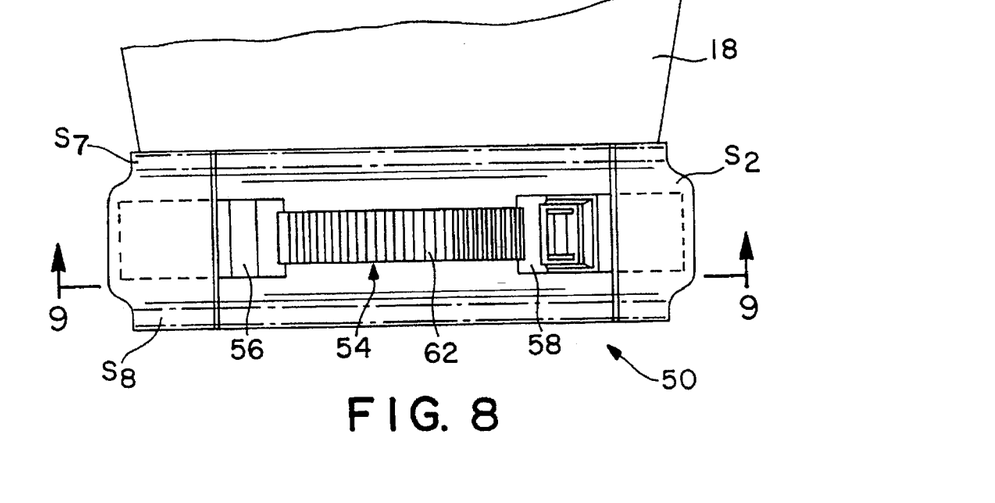
FIG. 8 is a plan view of a proximal end portion of the surgical apparatus of FIG. 1 with an integral tie clamp cuff according to the invention.

A method of using the surgical apparatus of FIG. 1, by way of illustration in a hand-assisted laparoscopic abdominal operation, is as follows. The abdomen is routinely prepared with antiseptics and dried, and a surgical template T such as shown in FIG. 7 is aligned on the abdomen relative to the umbilicus according to indicia printed on the template. Using a skin marker pen, incision and trocar/cannula puncture sites #1 and #2 as noted on the template are traced on the abdomen. The template T is removed and a transparent incise drape D adhered to the abdomen area. A muscle-split is made with a scalpel at the incision site, fat extracted if necessary, and the peritoneum incised. Protector 12 is placed in wound W by squeezing O-ring 14 into a tight ellipse and inserting it lengthwise through the incision until O-ring 14 expands inside the peritoneum and O-ring 16 overlaps the outside of drape D around the wound.

The surgeon's hand, which may be lubricated with any extracted fat, is inserted through wound protector 12 into the abdominal cavity for guiding trocars/cannulas $C_1$ and $C_2$ safely around internal organs as they are inserted at the sites indicated. When cannulas are in place, the hand is removed and surgical apparatus 10 is placed with fenestration over the wound. The hand is re-inserted through cuff 20 into sleeve 18 for drawing outer O-ring 16 through opening 24 and allowing it to expand inside sleeve 18 around the opening. Strips 30 are then peeled off of adhesive 28 enabling flange 26 to be pressed onto incise drape D with the entry opening of sleeve 18 oriented according to a surgeon's preference.

With the hand passed through cuff 20, inflator 22 is operated to seal around the surgeon's forearm. An insufflator is then connected to one of cannulas $C_1$ or $C_2$ to create pneumoperitoneum, and a telescope and other laparoscopic instruments inserted through the lumens as needed.

The hand may then be removed or re-inserted in sleeve 18 during the surgery with no significant loss of insufflating pressure in the abdominal cavity. Of course, if an organ or tissue suspected of infection is removed from the abdominal cavity, surgical apparatus 10, wound protector 12 and gloves should be replaced before re-entering the abdominal cavity to avoid cross-contamination.

Upon completing an operation, insufflation may be discontinued and the abdominal cavity depressurized. Wound protector 12 is simply removed by inserting a finger through its opening and gripping one edge of O-ring 14 and pulling it through the wound. The wound may now be closed according to conventional procedures.

Other types of structures may be utilized as the second sealing means in the present invention. Referring to FIGS. 8–12, there is shown another entry sealing means for the surgical apparatus of FIG. 1. Sleeve 18 includes a tie clamp cuff indicated generally by the reference number 50 comprising a cover strip 52 with edges heat-sealed along parallel spaced seams $S_7$ and $S_8$ to a proximal end portion of sleeve 18. The ends of strip 52 are spaced apart and form with sleeve 18 a covered track for sliding a tie 54 lengthwise. Tie 54 includes a finger grip 56 and a latch 58 which are exposed between the ends of strip 52 and are connected by a U-shaped strip 60 in the covered track. The two sides of strip 60 have serrated ends 60a projecting toward sleeve 18 to provide greater flexibility for closing tie 54 around an arm or instrument. An elastic pad 64, preferably of plastic foam, is lined between the tips of serrated ends 60a and the opposed end portion of sleeve 18 for insuring a continuous and positive seal when tie 54 is tightened around the arm.

Figures 10, 11:
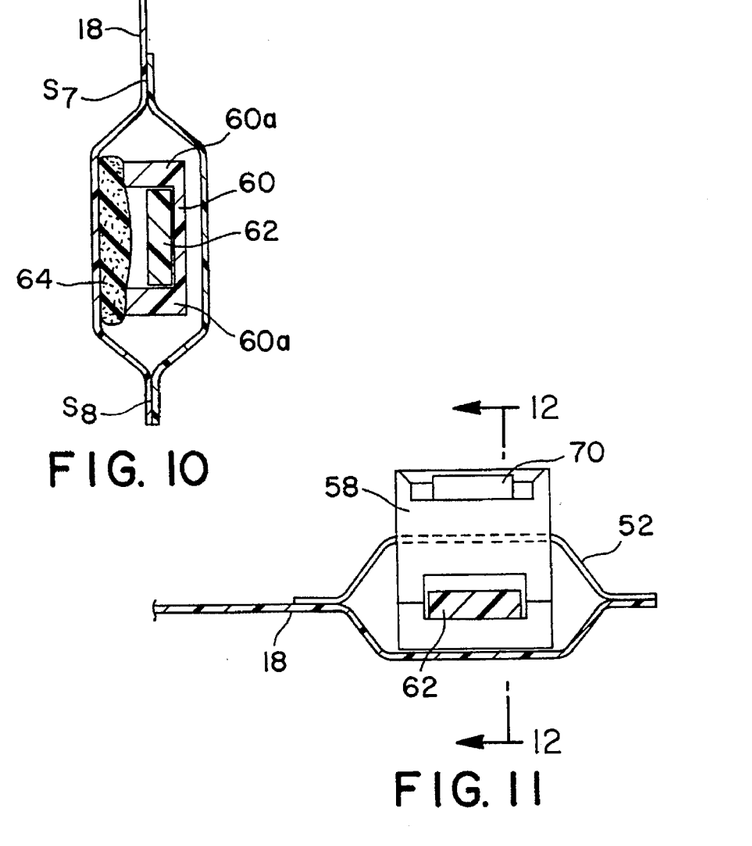
FIG. 10 is a radial cross section of the tie clamp cuff taken along the line 10—10 of FIG. 9.
FIG. 11 is an enlarged end view of a latch of the tie clamp cuff taken along the line 11—11 of FIG. 8.
Figure 12:
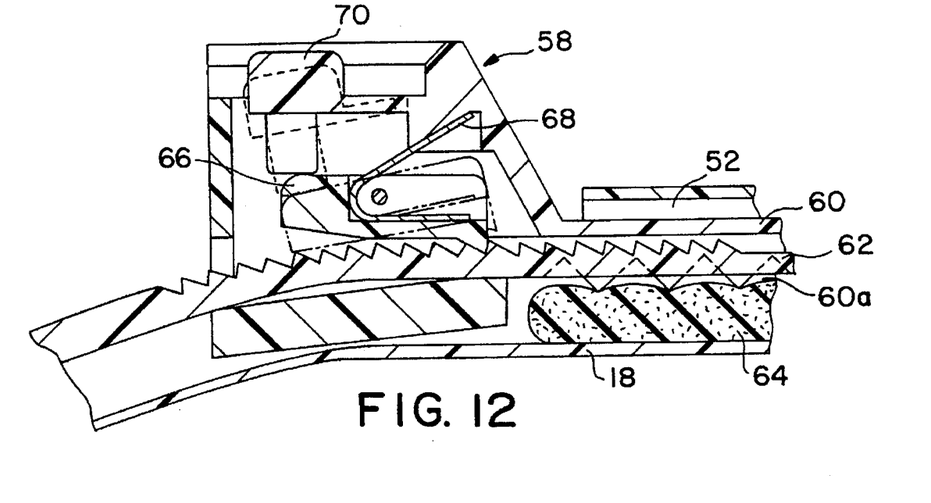
FIG. 12 is a view in cross section of the latch taken along the line 12—12 of FIG. 11.

As better illustrated in FIGS. 11 and 12, tie 54 is tightened by ratchetting a sawtooth leader 62 extending from grip 56 through a latch 58. A pawl 66 in the latch, urged by spring 68, engages a sawtooth of leader 62 to prevent loosening. To effect instant release of tie 54, a cantilevered pushbutton 70 acts against the force of spring 68 to rotate pawl 66 out of engagement to effect instant release of tie 54.

Figure 9:
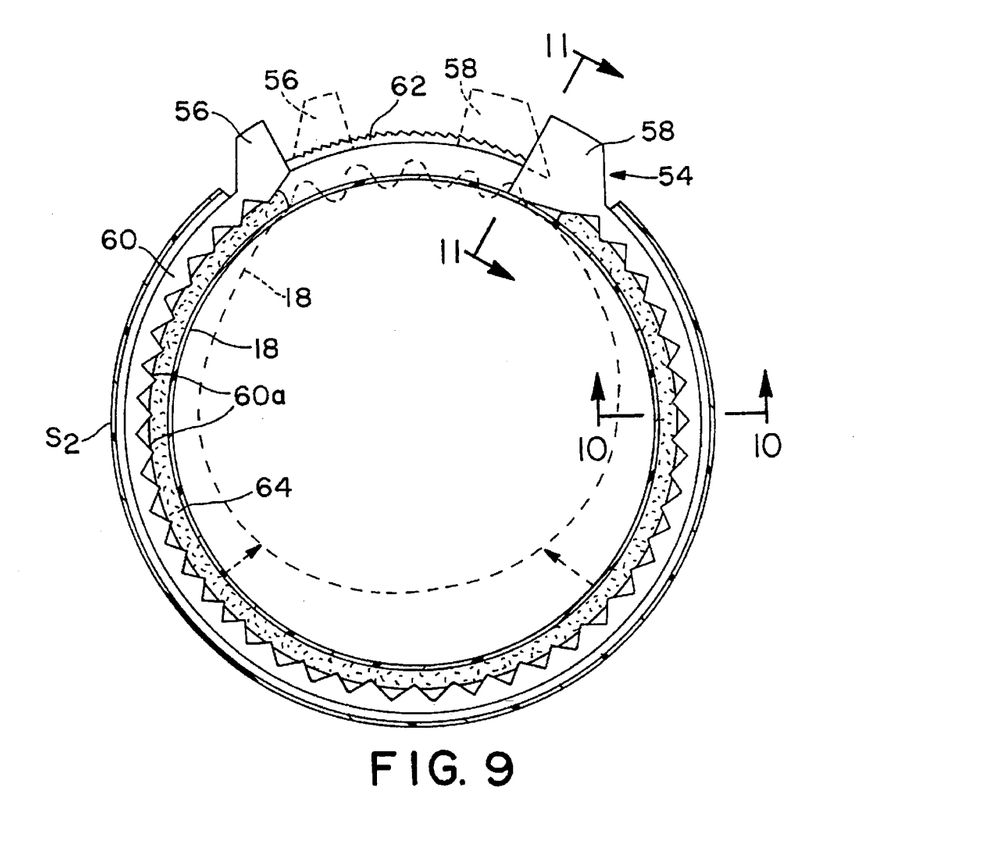
FIG. 9 is a view in transverse cross-section of the tie clamp cuff taken along the line 9—9 of FIG. 8.

As shown in dotted outline in FIG. 9, when a grip 56 and latch 58 are squeezed toward each other while a surgeon's arm is in cuff 50, tie 54 causes the portion of sleeve 18 between the grip and latch to fold pleat-like as the remaining portion constricts and presses against the surgeon's arm. Pad 64 distributes the pressure more evenly to ensure a good seal.

The embodiment of FIGS. 1–12 represent the most preferred embodiment for carrying out the invention, because the surgeon may readily insert and withdraw his hand several times during the course of surgery. Thus, the FIG. 1–12 embodiment is particularly useful in complex procedures that may require frequent change of instruments.

Figure 13:
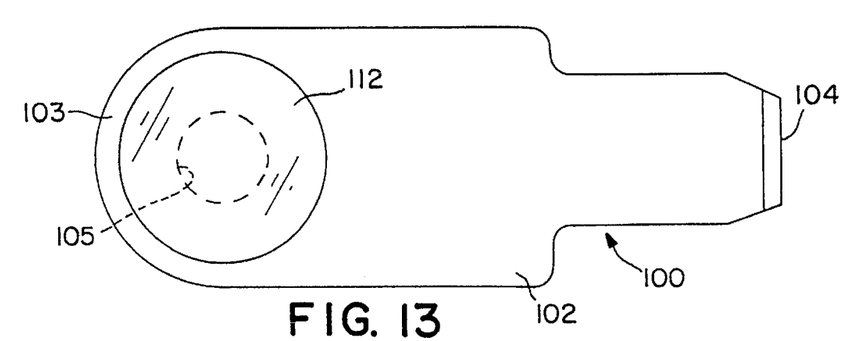
FIG. 13 is a plan view of another embodiment of the surgical apparatus with clear passage between entry and exit openings according to the invention.
Figure 14:
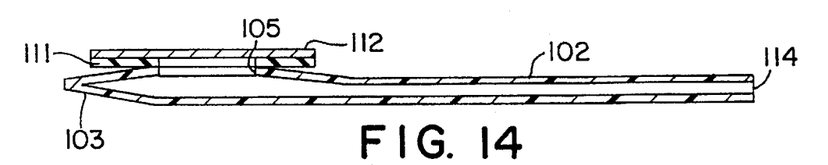
FIG. 14 is a view in longitudinal cross section of the surgical apparatus of FIG. 13.

For less complicated procedures, a version of the invention which does not have all of the features of the embodiments of FIGS. 1–12 may be utilized effectively. To this end, FIGS. 13 and 14 represent such an embodiment of a surgical apparatus 100 according to the invention. This apparatus 100 of this embodiment comprises a generally elongate cylindrical sleeve 102 of flexible gas-impermeable material like sleeve 18 of FIG. 1 which is closed at a distal end 103 and open at a proximal opposite end 104. An entry opening 114 at end 104 enables a surgeon's hand or surgical instrument to be introduced into sleeve 102. Near distal end 103 there is an exit opening 105 in continuous communication with entry opening 114. A flange 111 is disposed coaxially relative thereto in sealing engagement with sleeve 102. A suitable pressure-sensitive adhesive material on the exposed face of flange 111 is protected by a peel-to-remove cover 112.

Figure 15:
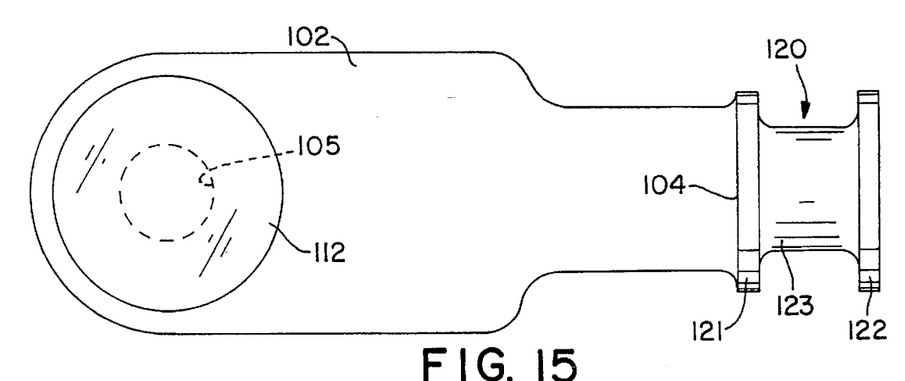
FIG. 15 is a plan view of the surgical apparatus of FIG. 13 with a twistable cuff according to the invention.

An entry sealing means, which for clarity is not illustrated in FIGS. 13 and 14, is indicated generally by a twistable cuff 120 in FIG. 15 integral with a proximal end 104. Cuff 120 includes a first flange 121 and a second flange 122 interconnected by a tubular sealing member 123 of flexible material.

Figure 16A:
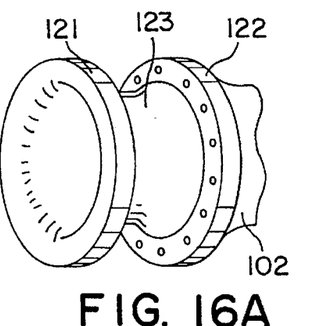
FIGS. 16A, 16B and 16C are perspective views of the twistable cuff of FIG. 15 in different positions of use.
Figures 16B, 16C:
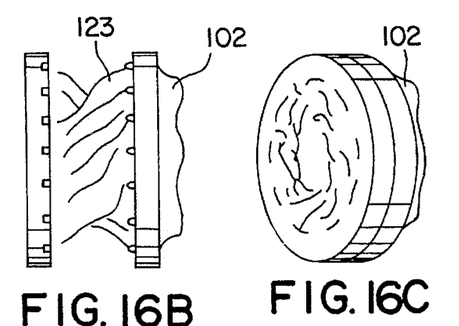
Figure 17:
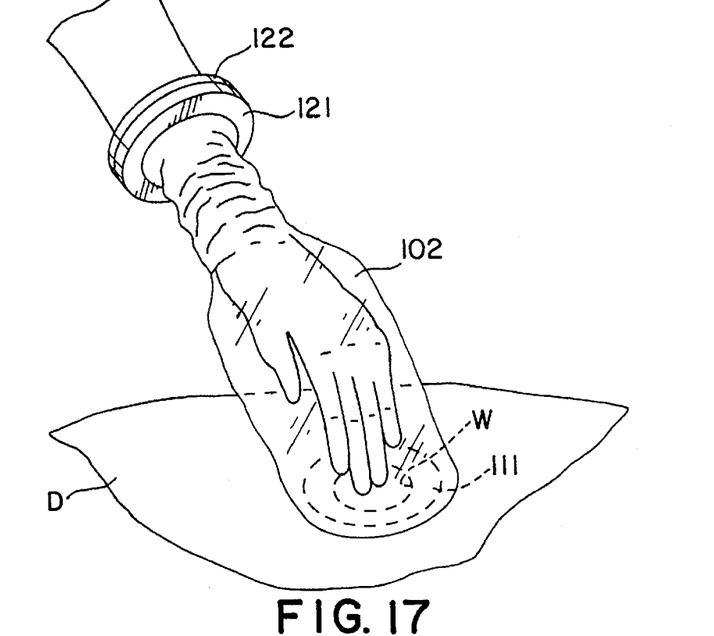
FIG. 17 is a perspective view of the surgical apparatus of FIG. 15 in actual use.

The surgical apparatus 100 of FIGS. 13–17 is used as follows. An incision is first made in the abdomen of a patient without cutting the peritoneum, and the wound hemostatically secured. Incise drape D is applied to the abdomen and an opening made in the drape. Protective cover 112 is removed and flange 111 adhesively bonded to the drape with sleeve exit opening 105 around the incision. If a hand is now inserted through entry opening 114, access to the incision in the abdomen can be achieved via the exit opening 105 as shown in FIG. 17. The interior of sleeve 102 and the abdominal cavity are placed in communication by cutting the peritoneum. Because the wrist of the surgeon's hand effectively occludes entry opening 114, insufflating gas in the abdominal cavity will inflate sleeve 102 like a balloon, preventing gas from escaping. Thus, the abdominal cavity remains in an insufflated condition while appropriate surgery or investigative procedures are carried out. The sealing arrangement at the entry opening of sleeve 102 in FIGS. 15–17 is enhanced by twistable cuff 120 which, by its nature, tends to fully interengage the wrist or arm of the surgeon.

Figure 18:
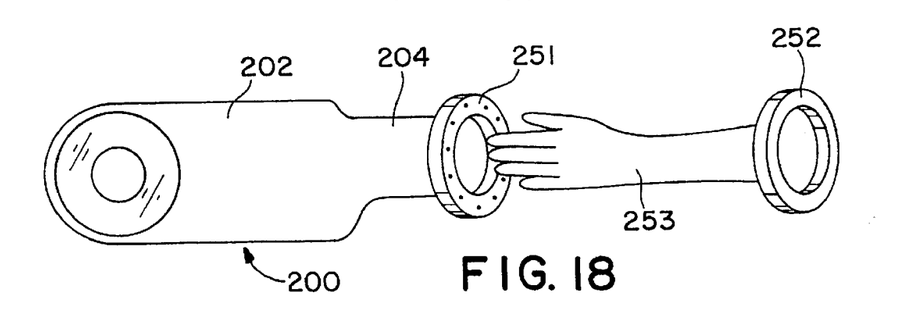
FIG. 18 is a perspective view of the surgical apparatus of FIG. 13 with a glove cuff at the entry opening according to the invention.

Another simplified embodiment is illustrated in FIG. 18. As seen therein, a surgical apparatus 200 similar in construction to apparatus 100 of FIGS. 13–17 is provided, except that a first flange 251 is integral with a proximal end 204 of a sleeve 202, and a second flange member 252 is integral with a surgeon's glove 253 in the region of the open end thereof. When the surgeon's arm with glove 253 passes into sleeve 202, flanges 251 and 252 are sealingly interengaged.

Figure 19:
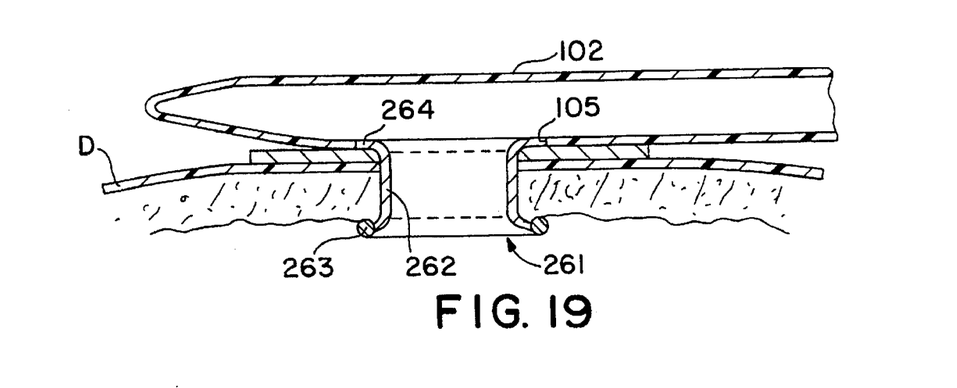
FIG. 19 is a view in longitudinal cross section of the distal end of the surgical apparatus of FIG. 13 with an integral wound protector according to the invention as applied to the abdomen of a patient.

FIG. 19 shows still another simplified embodiment of a surgical apparatus similar in construction to apparatus 100 of FIGS. 13–17 except sleeve 102 includes a wound protector 261 which is sealingly connected to the exit opening around the site of the incision in the abdomen. Protector 261 includes a tubular member 262 terminating at opposite ends with an inner ring 263 insertable through the incision, and an outer ring 264 peripherally connected to exit opening 105 in sleeve 102. Protector 261 is of the same type material as sleeve 102. Following incision, but before using the apparatus, ring 263 is inserted through the incision, and flange 111 adhesively attached to a drape D.

Some of the many novel features and advantages of the invention should now be readily apparent. Because hand-assisted laparoscopic techniques allow a surgeon to make only a relatively small incision, the trauma to the patient is minimized. There is less risk of damage to the immune system, healing time is shortened as well as the length of a hospital stay. A wider range of operations can be performed using an apparatus according to the invention. Conventional hand surgery in combination with laparoscopic techniques considerably simplifies procedures enabling them to be readily performed by a surgeon with minimal additional training. This is because the transition to hand-assisted laparoscopic surgery is relatively easy for a surgeon who is already trained in conventional hand surgery.

Additionally, or alternatively, an adhesive-backed flange may be placed around the exit opening of the sleeve, and in some cases adhesive may be applied to the patient around the area of the incision where the sealing flange is to be attached. Either or both adhesive may be covered by sterile wrapping material through which the incision can be made; and either or both layers of adhesive may be provided with peel-to-remove covers. A unique cuff for design is also provided which enables a surgeon to quickly seal or release his arm or a surgical instrument extending through an entry opening of a surgical enclosure. It is also contemplated that the sleeve may be easily modified to accommodate the use of both arms if required.

It will be understood, of course, that changes in details, steps and arrangement of parts which have been herein described and illustrated in order to explain the nature of the invention, may be made by those skilled in the art within the principle and scope of the invention as expressed in the appended claims.

We claim:

1. Apparatus for use in minimally invasive surgery through a wound into an insufflated cavity, comprising:

an outer sleeve of gas-impermeable supple material having an entry opening at a proximal end thereof and an exit opening at a distal end thereof;

first sealing means adapted to seal the exit opening gastightly around the wound in a patient; and second sealing means adapted to seal the entry opening gastightly around a surgeon's arm received therein and create thereby a gastight chamber in said outer sleeve when a surgeon's arm is operatively received in said sleeve;

whereby the sleeve cooperates with the first and second sealing means to enable the surgery to be performed under insufflatable conditions.

2. Apparatus according to claim 1 further comprising:
   third sealing means interposed in said sleeve between said first and second sealing means adapted to maintain the gastight chamber with the wound when said second sealing means is breached.

3. Apparatus according to claim 2 wherein:
   said third sealing means includes an inner sleeve having a proximal end sealingly joined at facing portions to said outer sleeve and a distal end forming a normally closed aperture which opens automatically in response to movement of an object from proximal to distal locations therethrough.

4. Apparatus according to claim 3 wherein:
   said third sealing means further includes a resilient means connecting the proximal end of said inner sleeve to said outer sleeve for biasing said aperture to a normally closed gastight position.

5. Apparatus according to claim 1 wherein:
   said first sealing means includes a flexible flange secured around said exit opening and having an exposed face adapted to attach around the wound.

6. Apparatus according to claim 5 further comprising:
   an adhesive coating on said exposed face adapted to adhere to said flange around the wound.

7. Apparatus according to claim 6 further comprising:
   a peel-off strip covering said adhesive coating.

8. Apparatus according to claim 1 wherein:
   said entry and exit openings are formed to accommodate a surgeon's hand and forearm.

9. Apparatus according to claim 1 wherein:
   said entry and exit openings are formed to accommodate instrumentarium.

10. Apparatus according to claim 1 wherein:
    said material is sufficiently flexible for effecting a wide range of arm movement at said entry opening relative to said exit opening.

11. Apparatus according to claim 1 further comprising:
    a wound protector means adapted to be inserted in the wound for simultaneously lining said exit opening and the wound, said protector including a pair of generally coaxial resilient rings contiguously connected to respective ends of a flexible tube, one of said rings being formed to compress said tube within said outer sleeve around said exit opening, and the other of said rings adapted to compress said tube around the internal side of the wound.

12. Apparatus according to claim 11 wherein said tube is made of a supple material effectively impermeable to gases and microorganism-bearing fluids.

13. Apparatus according to claim 12 wherein:
    said tube is adapted to be in contiguous contact with the wound.

14. Apparatus according to claim 1 wherein said second sealing means comprises:
    an inflatable tube fixed around the proximal end of said outer sleeve; and
    an elastic inflator operatively connected to said tube adapted to inflate said tube in compression around the surgeon's arm or instrument.

15. Apparatus according to claim 1 wherein said second sealing means comprises:
    a track formed around the proximal end of said outer sleeve;

a clamp tie having a U-shape strip adapted to slide in said track with an exposed finger grip at one end and an exposed latch at the other end, and a sawtooth leader adapted to slide in said strip extending from said grip for engaging said latch.

16. Apparatus according to claim 15 wherein said clamp tie further comprises:

an elastic pad interposed between said strip and said outer sleeve adapted to enhance contiguity of engagement between said outer sleeve and the surgeon's arm.

17. Apparatus according to claim 1 wherein:

said second sealing means includes a pair of flanges interconnected on a common axis by a supple tube, said flanges being relatively adjustable about said axis for twisting said tube into a constricting position around an object.

18. Apparatus according to claim 17 wherein;

said flanges include means for locking said flanges together in the constricting position.

19. Apparatus according to claim 1 wherein:

said second sealing means includes a first flange secured around said entry opening, a surgical glove for inserting into said outer sleeve through said first flange, and a second flange secured around the opening of said glove for sealing attachment to said first flange.

20. Apparatus for use in hand-assisted minimally-invasive surgery in a sufflatable body cavity having an outer surface, comprising:

an elongate flexible sleeve having an end portion adapted to be positioned adjacent the body cavity and a proximal end portion adapted to be positioned away from the body;

means defining an exit opening laterally of said flexible sleeve adjacent to said distal end portion;

means defining an entry opening co-axially of said flexible sleeve at said proximal end portion;

first sealing means carried by said sleeve and surrounding said exit opening and adapted to engage said body outer surface;

second sealing means carried by said sleeve and surrounding said proximal end portion adapted to seal gastightly a surgeon's arm; and means in said sleeve between its distal and proximal end portions providing a normally-closed flexible valve adapted to open upon insertion of the surgeon's hand toward the distal end portion of the sleeve and automatically close gastightly upon withdrawal of the surgeon's hand, said valve providing a third sealing means co-operable with said first sealing means to define a substantially gastight chamber in communication with said exit opening;

whereby the surgeon can readily insert and withdraw the hand from the body cavity in the course of surgery without significant loss of pressure in the body cavity when sufflated.

21. Apparatus according to claim 20 wherein said normally closed valve is of the duckbill type formed by at least one flexible panel secured to said sleeve and providing an aperture at a location adjacent to said exit opening.

22. Apparatus according to claim 21 including resilient means carried by said sleeve for biasing said at least one panel in a direction to close said aperture.

23. Apparatus according to claim 22 wherein said valve includes another panel like said first mentioned panel and juxtaposed in said sleeve therewith for cooperating therewith defining an elongate slot in said aperture.

24. Apparatus according to claim 20 wherein said means defining an exit opening includes an annular flange having an adhesive coating adapted to secure the sleeve to the body outer surface with the sleeve extending alongside the body.

25. Apparatus according to claim 20 including a flexible, tubular wound protector depending from said means providing said exit opening adapted to be inserted into a wound formed in said outer surface, said wound protector including a flexible membrane mounting annular elastic rings at opposite ends.

26. Apparatus according to claim 20 wherein said proximal end second sealing means is adapted to engage gastightly the periphery of the surgeon's arm when the hand is inserted in the sleeve.

27. Apparatus for use in hand-assisted minimally invasive surgery in a gas sufflatable body, comprising:

an elongate flexible sleeve having a lateral exit opening at one location and an axial entry opening at another location;

first means adapted to seal gastightly said sleeve around said exit opening to a body surface undergoing minimally invasive surgery;

second means adapted to seal gastightly said sleeve around a surgeon's arm adjacent to said entry opening; and means providing a duckbill check valve in said sleeve for preventing gas flow from said exit opening to said entry opening when said second sealing means is unsealed; whereby a surgeon may insert and withdraw the hand through the exit opening without significantly affecting gas pressure in the sufflated body.

28. Surgical apparatus for use in minimally invasive surgery for introducing a hand or instrument through a wound into an insufflated cavity comprising:

protective sleeve means of gas-impermeable material having a distal end adapted to be inserted through the wound for overlapping the lower edge thereof, and a proximal end formed to extend out of the wound;

an inside sealing ring, operatively connected to said sleeve means in proximity to the distal end, adapted to self-seal gastightly around the inside of the wound;

an outside sealing ring, operatively connected to said protective sleeve means in proximity to the proximal end thereof and forming with said first sealing means a gastight chamber in said protective sleeve means and adapted to seal gastightly around the outside of the wound;

an elongate gas-impermeable supple sleeve extending laterally of said outside sealing ring; and means providing a gastight-seal on said elongate sleeve at an end thereof remote from said outside sealing ring; whereby the wound is protected by the protective sleeve while insufflation gas is contained within the elongate sleeve.

29. Surgical apparatus according to claim 28 wherein:

said sleeve means includes a tubular portion closely conforming to the wound surface.

30. Surgical apparatus according to claim 28 wherein:

said first sealing means includes a normally closed resilient member formed to prevent gas flow from the cavity into the chamber.

31. Surgical apparatus according to claim 28 further comprising:

a resilent ring affixed around the distal end and adapted to expand beyond the edge of the wound when the distal end is fully inserted in the wound.

\* \* \* \* \*